US00PP25661P2

(12) United States Plant Patent
Lannes

(10) Patent No.: US PP25,661 P2
(45) Date of Patent: Jun. 30, 2015

(54) ***HIBISCUS* PLANT NAMED 'LANDRASOS'**

(50) Latin Name: *Hibiscus rosa-sinensis*
Varietal Denomination: Lanbrasos

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 182 days.

(21) Appl. No.: 13/987,548

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu
(74) *Attorney, Agent, or Firm* — Penny J. Aguirre

(57) ABSTRACT

A new cultivar of *Hibiscus* named 'Lanbrasos', characterized by its large flowers that are dark red in color with a darker eye zone, its short leaf internode lengths, its very dark green foliage, its good self-branching, and its very vigorous growth habit.

2 Drawing Sheets

Botanical classification: *Hibiscus rosa-sinensis*.
Cultivar designation: 'Lanbrasos'.

BACKGROUND OF THE INVENTION

The present invention relates to a new and distinct cultivar of *Hibiscus* plant of hybrid origin, botanically known as *Hibiscus rosa-sinensis* 'Lanbrasos' and will be referred to hereafter by its cultivar name, 'Lanbrasos'. 'Lanbrasos' is a new cultivar of tropical *hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2006 between 'Helene Rouge' (not patented) as the female parent and 'Holiday Rouge' (not patented) as the male parent. 'Lanbrasos' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lanbrasos'. These attributes in combination distinguish 'Lanbrasos' as a new and distinct cultivar of *Hibiscus*.

1. 'Lanbrasos' exhibits large flowers that are dark red in color with a darker eye zone.
2. 'Lanbrasos' exhibits short leaf internode lengths.
3. 'Lanbrasos' exhibits very dark green foliage.
4. 'Lanbrasos' exhibits good self-branching.
5. 'Lanbrasos' exhibits a very vigorous growth habit.

The female parent of 'Lanbrasos', 'Helene Rouge', differs from 'Lanbrasos' in having smaller flowers that are lighter red in color, in commencing bloom later in the season, and in having less self-branching. The male parent of 'Lanbrasos', 'Holiday Rouge', differs from 'Lanbrasos' in having smaller flowers that are lighter red in color and in having less self-branching. 'Lanbrasos' can also be most closely compared to the cultivars 'Arionicus' (U.S. Plant Pat. No. 22,746) and 'Marseille' (not patented). Both are similar to 'Lanbrasos' in having flowers that are red in color. 'Arionicus' differs from 'Lanbrasos' in having a smaller eye zone that is lighter in color with pink stripes, in having longer leaf internodes, and in having less self-branching. 'Marseille' differs from 'Lanbrasos' in having flowers that are smaller with orange tones and a center zone that is lighter red in color.

BRIEF DESCRIPTION OF THE DRAWING

The accompanying colored photograph illustrates the overall appearance and distinct characteristics of the new *Hibiscus*. The photographs were taken of a six month-old plant of 'Lanbrasos' as grown in a one-gallon container in a greenhouse in Malause, France.

The photograph in FIG. 1 provides a side view of 'Lanbrasos' in bloom.

Figure 1:
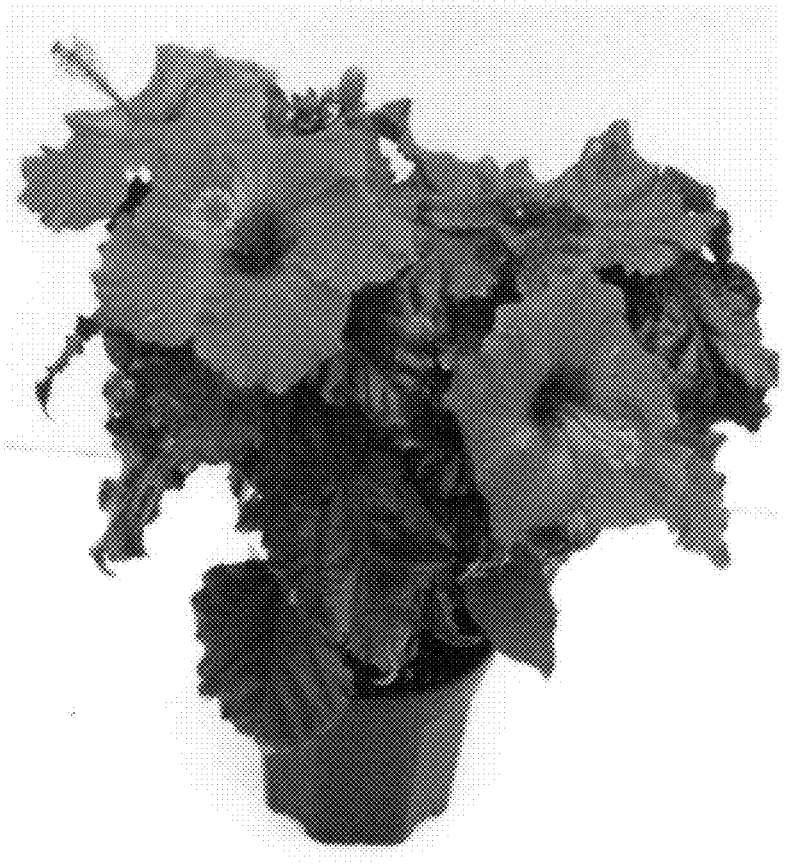
Figure 2:
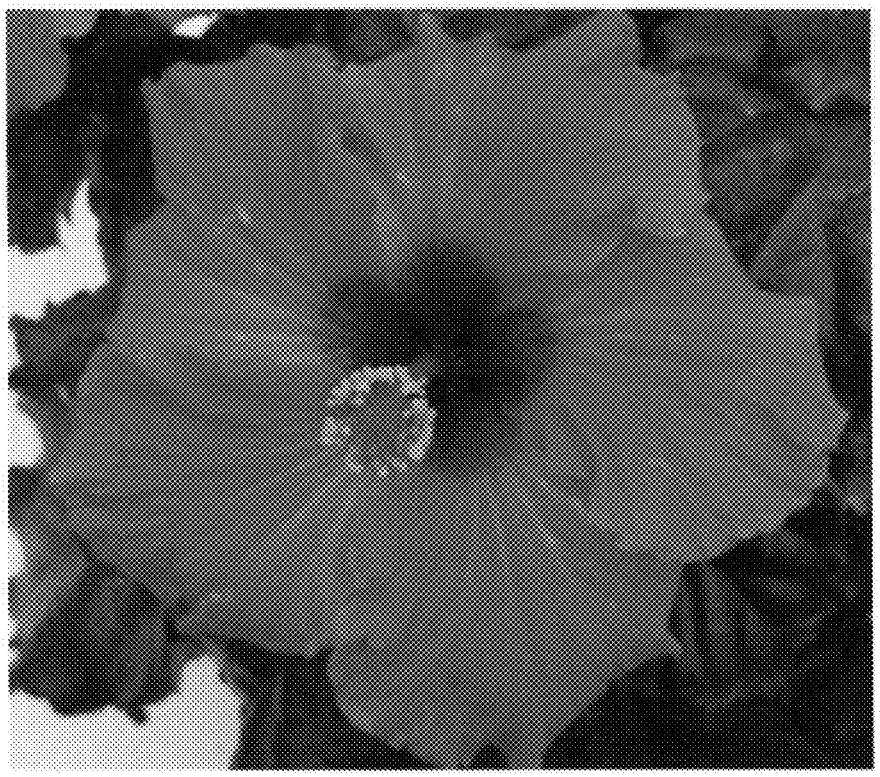

The photograph in FIG. 2 provides a close-up view of a flower of 'Lanbrasos'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 8 month-old plants of the new cultivar as grown in two-quart containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Continuously through summer in Grand Saline, Tex. and Malause, France.

*Plant type*.—Tropical evergreen shrub.

*Plant habit*.—Upright and slightly spreading, compact.

*Height and spread*.—Reaches 35 to 45 cm in height and 30 to 40 cm in spread.

*Hardiness*.—At least in U.S.D.A. Zones 9 to 11.

*Diseases*.—Not susceptible or resistance to diseases has been observed.

*Root description*.—Fibrous roots.

*Propagation*.—Stem cutting.

*Growth rate*.—Very vigorous.

Stem description:

*Shape*.—Slightly oval.

*Stem color*.—New growth; 138A, maturing wood; 191A, mature wood; 197A with striations of 197D.

*Stem size*.—Main stems; an average of 4.5 cm in length and 9 mm in width, lateral stems; an average of 17.5 cm in length and 4 mm in diameter.

*Stem surface*.—New growth; very sparse hairs, maturing wood; very sparse hairs, mature wood; finely striated.

*Stem aspect*.—Held upright to an average angle of 10° (0°=vertical).

*Stem strength*.—Strong.

*Branching*.—Self-branching, an average of 1 main stem and 5 lateral branches per main stem in a gallon container.

*Internode*.—Average of 4.5 cm.

Foliage description:

*Leaf shape*.—Ovate.

*Leaf division*.—Simple.

*Leaf base*.—Rounded.

*Leaf apex*.—Acute.

*Leaf venation*.—Pinnate, 141B on upper surface and 143A on lower surface.

*Leaf margins*.—New leaves; smooth, mature leaves; serrate and wavy.

*Leaf attachment*.—Petiolate.

*Leaf arrangement*.—Alternate.

*Leaf orientation*.—Held downward.

*Leaf aspect*.—Slightly cupped inward to flat.

*Leaf surface*.—Upper surface glabrous and glossy, lower surface very sparsely pubescent and satiny.

*Leaf color*.—Young and mature leaves upper surface N134A, lower surface 143A.

*Leaf size*.—Average of 11.5 cm in length, and 9.0 cm in width.

*Leaf quantity*.—About 4 leaves per lateral branch 17.5 cm in length.

*Petioles*.—Average of 4.0 cm in length and 3.8 mm in diameter, 137A in color, finely pubescent surface.

Flower description:

*Inflorescence type*.—Flowers are solitary.

*Lastingness of flowers*.—About 1 day, self cleaning.

*Flower size*.—An average of 6 cm in depth and 12 cm in diameter.

*Flower fragrance*.—None.

*Flower shape*.—Rotate.

*Flower number*.—Average of 2 per lateral stem at one time, continuously produces throughout the summer.

*Flower aspect*.—Upright and horizontal when fully open.

*Flower bud*.—Elliptic in shape, an average of 3 cm in length and 2 cm in width, color a blend of N144A and 60B, apex (petal portion); 60B.

*Flower attachment*.—Peduncle.

*Petal number*.—5.

*Petal shape*.—Orbicular.

*Petal color*.—Upper surface when opening and fully opened; 46B with veins NN155D near eye zone and eye zone 187A, lower surface when opening and fully opened; 45D with a blend of 11A on the right side of the petal and a spot on the base.

*Petal surface*.—Both surfaces smooth and dull on upper portion and satiny near base.

*Petal margins*.—Slightly wavy.

*Petal apex*.—Rounded.

*Petal base*.—Cuneate, slightly oblique and adnate to base of style.

*Petal size*.—Average of 7 cm in length and 5 cm in width.

*Sepal number*.—5.

*Sepal shape*.—Elliptic.

*Sepal margin*.—Entire.

*Sepal size*.—Average of 3 cm in length and 1 cm in width.

*Sepal aspect*.—Upright, lower 60% fused.

*Sepal surface*.—Outer surface puberulent, inner surface glabrous and glossy.

*Sepal apex*.—Cuspidate.

*Sepal base*.—Fused.

*Sepal color*.—Young and mature outer and inner surface; a blend of 144A and 145A.

*Calyx*.—Campanulate in shape, average of 3 cm in length and 1.5 cm in diameter.

*Peduncles*.—An average of 5 cm in length and 3 mm in diameter, strong, average angle is upright to 45°, 149A in color very sparsely pubescent surface.

*Pedicels*.—Not present, flowers are solitary from terminal leaf axils.

*Bracts*.—Average of 7 bracts held upright surrounding sepals, oblong in shape, apiculate apex, truncate base, average of 2 cm in length and 5 mm in width, a color between 137B in color on inner and outer surface, surface is slightly pubescent on inner and outer surface.

Reproductive organs:

*Gynoecium*.—1 pistil, about 7.5 cm in length, stigmas; 5, club-shaped, and mixed 46A in color with style arms 47B in color, 1 cm in length, and pubescent, style; 6 cm in length and 46B, base is 187A, ovary; oblong in shape, 1 cm in length and 1 cm in width, 11C in color and completely covered by the base of the pistil style.

*Androecium*.—Stamens; average of 50, stamens are clustered and implanted into upper portion of style, anthers; dorsifixed and orbicular in shape, 1 mm in diameter, and 14C in color; filament; 5 mm in length, 0.3 mm in width, and 46B in color, pollen; moderate in quantity and 14C in color.

*Fruit/seeds*.—None observed.

It is claimed:

1. A new and distinct cultivar of *Hibiscus* plant named 'Lanbrasos' as herein illustrated and described.

* * * * *

UNITED STATES PATENT AND TRADEMARK OFFICE

CERTIFICATE OF CORRECTION

PATENT NO. : PP25,661 P2
APPLICATION NO. : 13/987548
DATED : June 30, 2015
INVENTOR(S) : Robert Lannes It is certified that error appears in the above-identified patent and that said Letters Patent is hereby corrected as shown below:

Title Page, Item (54) Title: change "HIBISCUS PLANT NAMED 'LANDRASOS' TO HIBISCUS PLANT NAMED 'LANBRASOS'

Signed and Sealed this
Fifteenth Day of September, 2015

Michelle K. Lee

Michelle K. Lee
*Director of the United States Patent and Trademark Office*